United States Patent
Legrain-Raspaud et al.

(10) Patent No.: US 9,198,940 B2
(45) Date of Patent: Dec. 1, 2015

(54) PROBIOTIC STRAINS FOR USE IN IMPROVING THE ENTERIC NERVOUS SYSTEM

(75) Inventors: Sophie Legrain-Raspaud, Limours (FR); Gianfranco Grompone, Paris (FR); Sandrine Capronnier, Villemoisson sur Orge (FR); Isabelle Chambaud, Issy les Moulineaux (FR); Tamara Smokvina, Orsay (FR); Marie-Christine Degivry, Le Plessis Robinson (FR); Biliana Lesic, Palaiseau cedex (FR); Michel Neunlist, Nantes (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 13/700,485

(22) PCT Filed: May 27, 2011

(86) PCT No.: PCT/IB2011/052344
§ 371 (c)(1),
(2), (4) Date: Mar. 11, 2013

(87) PCT Pub. No.: WO2011/148355
PCT Pub. Date: Dec. 1, 2011

(65) Prior Publication Data
US 2013/0195822 A1    Aug. 1, 2013

(30) Foreign Application Priority Data
May 28, 2010   (WO) .................. PCT/IB2010/001534

(51) Int. Cl.
A61K 35/74     (2015.01)
A61K 35/747    (2015.01)
A23L 1/30      (2006.01)
A61K 35/745    (2015.01)

(52) U.S. Cl.
CPC ............. *A61K 35/747* (2013.01); *A23L 1/3014* (2013.01); *A61K 35/74* (2013.01); *A61K 35/745* (2013.01); *A23V 2002/00* (2013.01); *A23Y 2220/00* (2013.01)

(58) Field of Classification Search
None
See application file for complete search history.

(56) References Cited

U.S. PATENT DOCUMENTS

2008/0107634 A1 *  5/2008  Mogna et al. ............... 424/93.45
2008/0199444 A1 *  8/2008  Cui ............................ 424/93.41
2008/0311080 A1 * 12/2008  Collins et al. ................ 424/93.2

FOREIGN PATENT DOCUMENTS

WO      WO 0202800 A1 *  1/2002
WO      2010/008272      1/2010

OTHER PUBLICATIONS

Jimenez, Treatment of Irritable Bowel Syndrome with Probiotics. An Etiopathogenic Approach at Last?, Revista Espanola de Enfermedades Digestivas, 101, pp. 553-564, 2009.
Parkes, Treating Irritable Bowel Syndrome with Probiotics: The Evidence, Proceedings of the Nutrition Society, 69, pp. 187-194, 2010.
Moayyedi, The Efficacy of Probiotics in the Treatment of Irritable Bowel Syndrome: A Systematic Review, British Medical AssociationGUT, 59, pp. 325-332, 2010.
Agrawal, Fermented Milk Containing the Probiotic Bifidobacterium Animalis, DN-173 010 (FM) Improves Abdominal Distension, Bloating and Transit in Irritable Bowel Syndrome with Constipation, Gastroenterology, 134, A-546, 2008.
Guyonnet, Effect of Fermented Milk Containing Bifidobacterium Animalis DN-173 010 on the Health-Related Quality of Life and Symptoms in Irritable Bowel Syndrome in Adults in Primary Care: A Multicentre, Randomized, Double-Blind, Controlled Trial, Alimentary Pharmacology & Therapeutics, 26, pp. 475-486, 2007.
Heuvelin, Mechanisms Involved in Alleviation of Intestinal Inflammation by Bifidobacterium Breve Soluble Factors, Plos One, 4, pp. E5184-1, 2009.
Thibault, Effects of Long-Term Consumption of a Fermented Infant Formula (with *Bifidobacterium breve* c50 and *Streptococcus thermophilus* 065) on Acute Diarrhea in Healthy Infants, Journal of Pediatric Gastroenterology and Nutrition, 39, pp. 147-152, 2004.
Chevalier, Activity-Dependent Regulation of Tyrosine Hydroxylase Expression in the Enteric Nervous System, Journal of Physiology, 586, pp. 1963-1975, 2008.

* cited by examiner

*Primary Examiner* — Allison Fox
*Assistant Examiner* — Michelle F Paguio Frising
(74) *Attorney, Agent, or Firm* — Morgan Lewis & Bockius

(57) ABSTRACT

The invention relates to the use of lactic acid bacteria, for use in modifying the enteric nervous system and more particularly in treating and/or preventing intestinal disorders such as constipation and/or irritable bowel disease.

23 Claims, No Drawings

PROBIOTIC STRAINS FOR USE IN IMPROVING THE ENTERIC NERVOUS SYSTEM

FIELD

The present invention relates to compositions comprising strains of lactic acid bacteria for use in modifying the enteric nervous system. Such compositions are especially suitable to treat and/or prevent intestinal disorders such as constipation and/or irritable bowel disease.

BACKGROUND

Irritable bowel syndrome (IBS) or spastic colon is a functional bowel disorder characterized by chronic abdominal pain, discomfort, bloating, and alteration of bowel habits in the absence of any detectable organic cause. In some cases, a low-grade gut inflammation was reported. Diarrhoea or constipation may predominate, or they may alternate (classified as IBS-D, IBS-C respectively). IBS may begin after an infection (post-infectious, IBS-PI), a stressful life event or onset of maturity without any other medical indicators. In IBS, routine clinical tests yield no abnormalities, though the bowels may be more sensitive to certain stimuli, such as balloon insufflation testing.

IBS is a very common condition affecting approximately 15% of the population at any one time. There are about twice as many women as men with this condition. IBS is a source of chronic pain, fatigue and other symptoms, and it increases a patient's medical costs, and contributes to work absenteism. Researchers have reported that the high prevalence of IBS, in conjunction with increased costs produces a disease with a high societal cost. It is also regarded as a chronic illness and can dramatically affect the quality of a sufferer's life.

A leading theory about the cause of IBS relates to the enteric nervous system (ENS). The enteric nervous system (ENS) is a subdivision of the peripheral nervous system (PNS) that directly controls gastro-intestinal (GI) functions and is embedded in the lining of the gastrointestinal system. It includes efferent neurons, afferent neurons, and interneurons. The structural and physiological functioning of the ENS is performed by glial cells (astrocytes). The ENS is organized into two major plexus with functional specific roles.

The myenteric plexus, located between the longitudinal and circular muscle, contains neurones mainly involved in the control of intestinal motility. Through intestinal muscles, the efferent or motor neurons control peristalsis and churning of intestinal contents. The motor neurons controlling motility are composed of two major classes:
- excitatory myenteric neurons liberating acetylcholine (referred to as Choline AcetylTransferase ImmunoReactive neurons ("ChAT-IR" or "ChAT" or "ChAT neurones" or "ChAT nerves") and/or substance P (SP) for contractions, and
- inhibitory myenteric neurons liberating nitric oxide (identified as Nitric Oxide Synthase neurons (NOS-IR)) and/or Vaso-active Intestinal Peptide (VIP) for relaxation.

Choline acetyltransferase EC 2.3.1.6 is an enzyme that is synthesized within the body of a neuron and transferred to the nerve terminal. The role of ChAT is to join Acetyl-CoA to choline, resulting in the formation of the neurotransmitter acetylcholine. Experimentally, effect on acetylcholine production is extrapolated from the determination of the number of ChAT neurons, typically an increase in the number of ChAT nerves is indicative of an increase of acetylcholine.

The submucosal plexus, located between the circular muscle and the mucosa, contains neurons mainly involved in the control of intestinal epithelial barrier (IEB) functions, such as paracellular permeability. In particular, activation of enteric neurones in the submucosal plexus decreases paracellular permeability, via the liberation of VIP, whereas acetylcholine (Ach) increases paracellular permeability, setting the basis of a fine 'tuning' of the IEB permeability by the ENS. Thus, concerning the neuronal control of paracellular permeability, the increase of VIP liberation by submucosal neurons increases IEB integrity while the increase of submucosal plexus ChAT neurons decreases IEB resistance.

Although there is at current no cure for IBS, there are treatments which attempt to relieve symptoms, including dietary adjustments, medication and psychological interventions.

Probiotics, in particular strains of lactic acid bacteria, are reported to be beneficial in the treatment and/or prevention of IBS. Examples of such disclosures are WO 2007/036230, WO 03/010297, and WO 2009/080800. However, the bacterial strains are selected for their effect on the immune system, on intestinal permeability or on the intestinal microbiota and not for their effect on improving the function of the ENS. WO 2008/064489 discloses the use of probiotics to block an intermediate conductance calcium dependent potassium current resulting in an anti-inflammatory effect. WO 2007/132359 discloses the use of *Lactobacillus* and a cannabinoid receptor agonist and/or an opioid receptor antagonist in relation to pain perception. WO 2006/032542 discloses the use of *Lactobacillus* for analgesic purposes. Kamm et al, 2004, Neurogastrointest. Motil 16: 53-60 disclosed effects of *S. boulardii* on decreasing calbindin-28 k (CALB) but not on other neuronal markers of the pig jejunum. Metugriachuk et al, 2006, Rejuvenation Res. 9: 342-345 disclose that a symbiotic preparation on motility of small and large intestine in old Wistar rats significantly increased the myoelectric activity of small intestine and colon, an increased mRNA expression of VIP, but no significant effect on VIP concentration.

Further research is therefore needed on individual strains of probiotic bacteria with a beneficial effect on the ENS for use in IBS, constipation and/or other disorders.

SUMMARY OF THE INVENTION

The inventors employed a new model system for screening and selecting strains of lactic acid bacteria and bifidobacteria which have an improved effect on the enteric nervous system (ENS). This model contains a (mono)layer of intestinal epithelial cells from human colon carcinoma and, on the basolateral side of the monolayer, a mixture of a primary culture of enteric nervous system cells including neurones from myenteric and submucosal plexus. Using this model the effects of food grade components, in particular strains of lactic acid bacteria and bifidobacteria, on the ENS could be assessed by measuring the effects of apical or luminal addition of these components on the expression of vaso-intestinal peptide (VIP) and/or ChAT releasing nerves on the basolateral side.

This model therefore allowed to screen and to select new strains of lactic acid bacteria and bifidobacteria for use in improving the function of the enteric nervous system. Such strains improve intestinal motility and peristalsis. With some strains the intestinal transit time can be reduced, which can address some conditions such as constipation. With some strains the intestinal transit time can be increased, which can address some conditions such as diarrhoea. VIP increasing strains also improve intestinal epithelial barrier integrity. Such strains are in particular useful and more efficacious than existing strains in prevention and/or treatment of IBS and/or constipation and other disorders associated with a decreased function of the ENS.

Increasing cholinergic phenotype, in particular the expression of ChAT neurons is of therapeutic interest in GI tract pathologies associated with inhibition of colonic transit. Using lactic acid bacteria or bifidobacteria selected to have an increasing effect on enhancing cholinergic expression, i.e. ChAT, in neurons are of therapeutical interest for constipated patients, and patients suffering from IBS-C. Therefore, one group of lactic acid bacteria or bifidobacteria strains of the present invention advantageously increases the number of ChAT nerves, which is indicative for an improved effect on intestinal motility, and especially is beneficial for IBS patients, in particular IBS-C patients, and patients suffering from constipation. This group is referred to as group B). Good motility requires a high number of ChAT nerves, which are responsible for contraction and have a prokinetic effect. In some interesting embodiments for this group the TEER levels are not decreased, since the IEB function and ability to relax the muscles is preferably not impaired. The subgroup according to these embodiments is referred to as group B3).

Increasing VIP beneficially improves relaxation of the muscles of the GI tract and improves IEB, which is beneficial for patients suffering from IBS or inflammatory bowel disease (IBD) and also for elderly people, infants, and obese people. For such subjects a good IEB function is better if not essential. Although patients suffering from IBS or IBD have an oversecretion of neuropeptides such as VIP, this is supposed to be an adaptative response of the ENS to control intestinal inflammation, to re-establish intestinal barrier functions and to increase neuroprotection. A group of lactic acid producing bacteria strains, in particular bifidobacteria, of the present invention advantageously increases VIP. This group is referred to as group A). In one embodiment the ChAT level is not increased. The group according to this embodiment is referred to as group A3). Accordingly the ChAT level can remain substantially unchanged or can decrease.

All the herein referred bacterial strains have been deposited, according to the Budapest Treaty, before CNCM ("Collection Nationale de Cultures de Microorganismes", 25 rue du Docteur Roux, Paris) as an International depositary authority.

Strains found with the screening method were belonging to group B) are DN_154_0067 (CNCM I-4320 filed May 19, 2010), DN_116_0047 (CNCM I-4317 filed May 19, 2010) and DN_119_0118 (CNCM I-4279 filed Feb. 25, 2010). Strains belonging to group A) are DN_173_010 (CNCM I-2494 filed Jun. 20, 2000), DN_156_0032 (CNCM I-4321 filed May 19, 2010), DN_156_007 (CNCM I-2219 filed May 31, 1999), and DN_121_0304 (CNCM I-4318 filed May 19, 2010). Strain DN_173_010 (CNCM I-2494 filed Jun. 20, 2000) has been disclosed in International application WO 02/02800 and strain DN_156_007 (CNCM I-2219 filed May 31, 1999) has been disclosed in International application WO 01/01785.

Compositions comprising at least one of these selected strains are therefore part of the invention. A composition comprising a mix of at least one strain belonging to group B) and at least one strain belonging to group A) is preferred. Such a mix will advantageously have an improved effect on motility by improving both contractions and relaxations and additionally have an advantageous effect on IEB function.

Thus, according to one aspect the invention concerns a composition comprising at least one strain of bacteria, preferably selected from the group consisting of lactobacilli and bifidobacteria, for use in:

A) increasing vaso-active intestinal peptide (VIP) levels of the enteric nervous system, or B) increasing Choline AcetylTransferase ImmunoReactive neurones (ChAT) levels of the enteric nervous system, or C) decreasing ChAT levels of the enteric nervous system.

According to one aspect the invention concerns a composition comprising at least one strain of bacteria selected from the group consisting of the following strains:

DN_156_0032 (CNCM I-4321 filed May 19, 2010) [A)-A3)],

DN_156_007 (CNCM I-2219 filed May 31, 1999) [A)-A3)],

DN_121_0304 (CNCM I-4318 filed May 19, 2010) [A)-A3)],

DN_116_0047 (CNCM I-4317 filed May 19, 2010) [B)-B3)],

DN_154_0067 (CNCM I-4320 filed May 19, 2010) [B)-B3)], and

DN_119_0118 (CNCM I-4279 filed Feb. 25, 2010) [B)-B3)], for use in:

treatment and/or prevention of an intestinal disorder, preferably treatment and/or prevention of an intestinal motility disorder, or treatment and/or prevention of a disorder selected form the group consisting of constipation and IBS-C, treatment and/or prevention of a disorder selected from the group consisting of diarrhoea, intestinal infection, IBS-D, IBS-PI, and IBD, or treatment and/or prevention of a disorder selected from the group consisting of IBS and IBD, or treatment and/or prevention of disorders found in elderly people, infants, or obese people.

According to one aspect the invention concerns a composition comprising at least one strain of bacteria selected from the group consisting of the following strains:

DN_156_0032 (CNCM I-4321 filed May 19, 2010) [A)-A3)],

DN_156_007 (CNCM I-2219 filed May 31, 1999) [A)-A3)],

DN_121_0304 (CNCM I-4318 filed May 19, 2010) [A)-A3)],

DN_116_0047 (CNCM I-4317 filed May 19, 2010) [B)-B3)],

DN_154_0067 (CNCM I-4320 filed May 19, 2010) [B)-B3)], and

DN_119_0118 (CNCM I-4279 filed Feb. 25, 2010)[B)-B3)], for use in administration to subjects suffering from a disorder selected from the group consisting of:

constipation, IBS-C, diarrhoea, intestinal infection, IBS-D, IBS-PI, IBD,

IBS, and disorders found in elderly people, infants, or obese people.

According to one aspect the invention concerns a composition as mentioned above for use in improving gastro-intestinal motility, improving intestinal peristalsis and/or decreasing intestinal permeability.

According to one aspect the invention concerns new strains of bacteria selected from the group consisting of:

DN_156_0032 (CNCM I-4321 filed May 19, 2010) [A)-A3)],

DN_121_0304 (CNCM I-4318 filed May 19, 2010) [A)-A3)],

DN_116_0047 (CNCM I-4317 filed May 19, 2010) [B)-B3)], and

DN_154_0067 (CNCM I-4320 filed May 19, 2010) [B)-B3)].

According to one aspect the invention concerns compositions comprising the new strains.

According to one aspect the invention concerns a composition comprising:
- at least one strain of bacteria selected from the group consisting of lactobacilli and bifidobacteria that B) increases ChAT levels in the enteric nervous system, and
- at least one strain of bacteria selected from the group consisting of lactobacilli and bifidobacteria that A) increases vaso-active intestinal peptide (VIP) levels in the enteric nervous system.

According to one aspect the invention concerns a method of selecting strains of bacteria, said method comprising the steps of:
- a) Arranging a coculture of intestinal epithelial cells and enteric neuronic cells, wherein said intestinal epithelial cell are present as a monolayer and wherein said enteric neuronic cells are present at the basolateral side of the monolayer,
- b) Adding strains of bacteria to the apical or luminal side of the monolayer of intestinal epithelial cells, preferably in an amount of about 4 to 400 bacterial cells per epithelial cell,
- c) Incubating the coculture with the strain of lactic acid bacteria,
- d) Preferably isolating the neuronic cells,
- e) Measuring the amount of VIP, ChAT, substance P, Nitrogen Oxide nerves, ATP and/or pituitary adenylate cyclase activating peptide (PACAP) produced by the neuronic cells and optionally additionally the TransEpithelial Electrical Resistance (TEER) of the intestinal epithelial cells layer.

In this method, the strain of bacteria preferably belongs to the group consisting of lactobacilli and bifidobacteria.

DETAILED DESCRIPTION

Definitions

In the present application the use of a compound or a composition is intended to cover the use itself, optionally with the connected intention, but also any communication associated to the compound or composition with commercial or legal consequences, for example advertisement, instructions or recommendation on the package of the compositions, instructions or recommendation on commercial support such as leaflets, brochures, posters, documentation filed in support to regulatory registrations for safety purpose, efficacy purpose, or consumer protection, for example at administrations such as EFSA in Europe.

In the present application groups of strains refer to strains that exhibit a specific property or set of properties. A specific strain can thus pertain to several groups. In the present application the term "or" is not exclusive.

In the present application a property such as VIP and/or ChAT is considered as substantially unchanged compared to a control if the variation does not exceed 10%, preferably 1% compared to the control.

Preferred Embodiments

In preferred embodiments, the composition is for use in:
- A3) increasing VIP, provided that ChAT is not increased, or
- B3) increasing ChAT, provided that VIP is not increased, Electrical Resistance (TEER) of the intestinal epithelial cells layer being not decreased or
- C3) decreasing ChAT, provided that VIP is not decreased, or
- C2) decreasing ChAT and decreasing VIP.

For example the composition of the invention can be used in:
- treatment and/or prevention of an intestinal disorder, preferably treatment and/or prevention of an intestinal motility disorder, or
- treatment and/or prevention of a disorder selected form the group consisting of constipation and IBS-C, or
- treatment and/or prevention of a disorder selected from the group consisting of diarrhoea, intestinal infection, IBS-D, IBS-PI, and IBD, or
- treatment and/or prevention of a disorder selected from the group consisting of IBS and IBD, or
- treatment and/or prevention of disorders found in elderly people, infants, and obese people.

In especially preferred embodiments, the compositions can:
- A) increase VIP levels of the enteric nervous system, and be used in treatment and/or prevention of an intestinal disorder, preferably treatment and/or prevention of an intestinal motility disorder, or
- B) increase ChAT levels of the enteric nervous system, and be used in treatment and/or prevention of a disorder selected form the group consisting of constipation and IBS-C, or
- C) decrease ChAT levels of the enteric nervous system, and be used in treatment and/or prevention of a disorder selected from the group consisting of diarrhoea, IBS-D, IBS-PI, IBD.

The strain of bacteria can for example be selected from the group consisting of the following strains:
- DN_173_010 (CNCM I-2494 filed Jun. 20, 2000) [A)-A3)],
- DN_156_0032 (CNCM I-4321 filed May 19, 2010) [A)-A3)],
- DN_156_007 (CNCM I-2219 filed May 31, 1999) [A)-A3)],
- DN_121_0304 (CNCM I-4318 filed May 19, 2010) [A)-A3)],
- DN_116_0047 (CNCM I-4317 filed May 19, 2010) [B)-B3)],
- DN_154_0067 (CNCM I-4320 filed May 19, 2010) [B)-B3)], and
- DN_119_0118 (CNCM I-4279 filed Feb. 25, 2010) [B)-B3)].

In one embodiment the strain of bacteria is selected from the group consisting of the following strains:
- DN_156_0032 (CNCM I-4321 filed May 19, 2010) [A)-A3)],
- DN_156_007 (CNCM I-2219 filed May 31, 1999) [A)-A3)], and
- DN_121_0304 (CNCM I-4318 filed May 19, 2010) [A)-A3)], and the composition is for use in:
- treatment and/or prevention of a disorder selected from the group consisting of IBS and IBD, or
- treatment and/or prevention of disorders found in elderly people, infants, or obese people.

In one embodiment the strain of bacteria is selected from the group consisting of the following strains:
- DN_116_0047 (CNCM I-4317 filed May 19, 2010) [B)-B3)],
- DN_154_0067 (CNCM I-4320 filed May 19, 2010) [B)-B3)], and
- DN_119_0118 (CNCM I-4279 filed Feb. 25, 2010) [B)-B3)], and the composition for use in treatment and/or prevention of a disorder selected from the group consisting of constipation and IBS-C.

In one embodiment the strain of bacteria is selected from the group consisting of the following strains:

DN__156__0032 (CNCM I-4321 filed May 19, 2010) [A)-A3)],

DN__156__007 (CNCM I-2219 filed May 31, 1999) [A)-A3)], and

DN__121__0304 (CNCM I-4318 filed May 19, 2010) [A)-A3)], and the composition is for use in:

A) increasing vaso-active intestinal peptide (VIP) levels of the enteric nervous system, preferably for use in A3) increasing VIP, provided that ChAT is not increased.

In a particular embodiment of this embodiment, the composition is for use in:

treatment and/or prevention of a disorder selected from the group consisting of IBS and IBD, or treatment and/or prevention of disorders found in elderly people, infants, or obese people.

In one embodiment the strain of bacteria is selected from the group consisting of the following strains:

DN__116__0047 (CNCM I-4317 filed May 19, 2010) [B)-B3)],

DN__154__0067 (CNCM I-4320 filed May 19, 2010) [B)-B3)], and

DN__119__0118 (CNCM I-4279 filed Feb. 25, 2010) [B)-B3)], and the composition is for use in:

B) increasing ChAT levels of the enteric nervous system, preferably B3) increasing ChAT, provided that VIP is not increased.

In a particular embodiment of this embodiment, the composition is for use in treatment and/or prevention of a disorder selected form the group consisting of constipation and IBS-C.

Further Details of Strains of Bacteria

As mentioned above the composition comprises at least one or two specific strains of bacteria, preferably lactic acid bacteria. They are preferably selected from the group consisting of the genus *Lactobacillus* and *Bifidobacterium, Lactococcus* and *Streptococcus*. The said specific strain of bacteria were found to be capable to affect VIP levels and/or to affect ChAT nerve levels in a coculture model representing the interaction between the intestine and the ENS.

A coculture model, described in more detail below, was used to in vitro select strains of lactic acid bacteria or bifidobacteria with these properties. 102 strains belonging to the genera *Lactobacillus, Streptococcus* or *Bifidobacterium* were screened.

Group B) strains with increased effect on ChAT will typically improve intestinal motility. Group B3) strains with increased effect on ChAT, excluding strains wherein VIP is not increased (i.e. VIP is substantially unchanged or VIP is decreased) represent a specific preferred embodiment. Strains of these groups are typically beneficial for treatment and/or prevention of a disorder selected form the group consisting of constipation and IBS-C. This might be of further particular interest for treatment and/or prevention of disorders found in elderly people, which can often suffer from constipation. Concerning increasing motility, strains increasing ChAT expression would be favoured. This property appears to be very rare. Interestingly, only three strains were found to increase statistically ChAT. These are referred to group B) or group B3) strains. Group B) or group B3) strains comprise strains DN__119__0118 (CNCM I-4279 filed Feb. 25, 2010), DN__154__0067 (CNCM I-4320 filed May 19, 2010) and DN__116__0047 (CNCM I-4317 filed May 19, 2010). Such strains beneficially improve motility, especially contractions. It is preferred that Electrical Resistance (TEER) of the intestinal epithelial cells layer be not decreased. Such a property can be indicative of a suitable barrier function. Strain DN__119__0118 (CNCM I-4279 filed Feb. 25, 2010) significantly decreased VIP levels, whereas the other two strains did not have a significant effect on VIP levels. Since a decrease in VIP may have an adverse effect on IEB it was examined with an in vitro model with a monolayer of intestinal epithelial cells whether incubation of this strain resulted in a decrease transepithelial electrical resistance (TEER). This turned out not to be the case, indicating that the IEB function is not impaired.

Concerning the relaxation of the muscles and reinforcement of IEB function, which is beneficial in IBS and IBD patients, strains would be favoured that increase VIP expression (which would have in addition anti-inflammatory effects). Such strains are referred to as group A) strains. In a preferred embodiment group A) strains do not increase ChAT expression (i.e. ChAT is substantially unchanged or ChAT is decreased). Such strains are referred to as group A3) strains. Strains of these groups are typically beneficial to treatment and/or prevention of a disorder selected from the group consisting of IBS and IBD, or to treatment and/or prevention of disorders found in elderly people, infants, or obese people. Group A) or group A3) strains comprise strains DN__173__010 (CNCM I-2494 filed Jun. 20, 2000), DN__156__0032 (CNCM I-4321 filed May 19, 2010), DN__156__007 (CNCM I-2219 filed May 31, 1999), DN__121__0304 (CNCM I-4318 filed May 19, 2010). It is interesting to note that all the strains having this property are bifidobacteria except one: DN__121__0304 (CNCM I-4318 filed May 19, 2010). Furthermore, using another in vitro model with a T84 monolayer and the transepithelial electric resistance (TEER) especially strains DN__173__010 (CNCM I-2494 filed Jun. 20, 2000), DN__156__007 (CNCM I-2219 filed May 31, 1999), DN__121__0304 (CNCM I-4318 filed May 19, 2010) and DN__156__0032 (CNCM I-4321 filed May 19, 2010) of group A) or A3) were found to have a protective effect on the IEB in the presence of LPS. Therefore, these particular strains are especially preferred.

According to one embodiment the strains allow decreasing ChAT levels of the enteric nervous system. The corresponding group of strains is referred to as group C). In a particular embodiment the strains allow decreasing ChAT, provided that VIP is not decreased (i.e. VIP is substantially unchanged or VIP is increased). This group is referred to as group C3). In a particular embodiment the strains allow decreasing ChAT with decreasing VIP. These strains are referred to as group C2). Strains of group C3) are typically beneficial to treatment and/or prevention of a disorder selected form the group consisting of diarrhoea, IBS-D. This might be of further particular interest for treatment and/or prevention of disorders found in elderly people, which can often suffer from diarrhoea. Strains of group C2) are typically beneficial to treatment and/or prevention of a disorder selected from the group consisting of diarrhoea, IBS-D, IBS-PI, and IBD. This might be of further particular interest for treatment and/or prevention of disorders found in elderly people which can often suffer from such conditions, especially diarrhoea.

The present invention also encompasses the use of the above mentioned strains, but also mutant strains or genetically transformed strains derived from any one of the parent strains still having activity on VIP and effecting ChAT nerves. These mutant or genetically transformed strains can be strains wherein one or more endogenous gene(s) of the parent strain has (have) been mutated, for instance to modify some of its metabolic properties (e. g. its ability to ferment sugars, its resistance to acidity, its survival to transport in the gastrointestinal tract, its post-acidification or its metabolite production). They can also be strains resulting from the genetic transformation of the parent strain by one or more gene(s) of interest, for instance in order to give to said strain additional physiological features, or to allow it to express proteins of therapeutic or vaccinal interest that one wishes to administer through said strains.

Preferably a mix of at least one strain belonging to group B), preferably group B3), and at least one strain belonging to group A), preferably group A3), is used. Such a mix will advantageously have an improved effect on motility as well as on IEB.

Co-Culture Model and Screening Assay

In one embodiment the present invention relates to a method of selecting strains of lactic acid bacteria, said method comprising the steps of:

a) Using a coculture of intestinal epithelial cells and enteric neuronic cells, wherein the intestinal epithelial cells are present as a monolayer and wherein the enteric neuronic cells are present at the basolateral side of the monolayer, b) Adding lactic acid bacteria or the apical or luminal side of the monolayer, preferably in an amount of about 4 to 400 bacterial cells per epithelial cell, c) Incubating the coculture with the lactic acid bacteria, d) Preferably isolating the neuronic cells, and e) Measuring the amount of at least one neurotransmitter selected from the group consisting of VIP, ChAT, substance P and Nitrogen Oxide, ATP, PACAP produced by the neuronic cells, and optionally additionally the TransEpithelial Electrical Resistance (TEER) of the intestinal epithelial cells layer.

In agreement with the peristaltic reflex the ENS contains hardwired circuits that consist of ascending excitatory motor neurons that release acetylcholine and substance P, which contracts smooth muscle through muscarinic receptors, and of descending inhibitory neurons that release a cocktail of transmitters, like NO, ATP, VIP and PACAP, all of which inhibit the circular muscle.

Cell Culture

A suitable way to set up the coculture with a monolayer of polarized intestinal epithelial cells is given in example 1 and is also described in J. Chevalier et al, 2008, J. Physiol. 586 1963-1975.

All intestinal epithelial cell cultures forming monolayers are suitable, such as Caco-2, T84, HT29, and TC7. Preferably T84 cells are used.

As primary enteric nerve system cells, preferably cells are isolated from non-human mammalian foetuses, preferably rodents, more preferably rats.

Preferably the bacteria strains tested are grown to late exponential phase in a suitable growth medium and washed. Preferably the bacteria are added to the apical side of the coculture at an amount of 4 to 400 bacteria/epithelial cell, more preferably 10 to 100 bacteria/epithelial cell, even more preferably 30 to 50 bacteria/epithelial cell. Preferably, as a control, no bacteria are added. Preferably, as a positive control 1 mM butyrate or 40 mM KCl is used.

Preferably the incubation step is performed at about 37° C. Preferably the incubation step takes 1 to 72 h, more preferably 2 to 36 h, even more preferably 4 to 12 h.

Preferably after co-incubation, the compartment containing epithelial cells and bacteria is removed and primary neuronal cells are incubated for 12 to 48 h, more preferably for 20 to 28 h in a humidified incubator containing 5% $CO_2$.

Preferably the amount of ChAT nerves versus total nerves is measured using immunohistochemical staining, using anti-neurone specific enolase (NSE) to count the total number of neurones and anti-choline acetyl transferase to count the ChAT nerves.

Preferably VIP is determined by ELISA after collecting the neuronal cells and extracting the proteins with the presence of a protease inhibitor cocktail.

Further Details about Compositions

The invention encompasses compositions with strains of bacteria which allow the above referenced uses or properties. The invention also encompasses compositions comprising one or more of the following strains (encompassing mutants or genetically transformed strains derived thereof):

DN_156_0032 (CNCM I-4321 filed May 19, 2010) [A)-A3)],

DN_156_007 (CNCM I-2219 filed May 31, 1999) [A)-A3)],

DN_121_0304 (CNCM I-4318 filed May 19, 2010) [A)-A3)],

DN_116_0047 (CNCM I-4317 filed May 19, 2010) [B)-B3)],

DN_154_0067 (CNCM I-4320 filed May 19, 2010) [B)-B3)], and

DN_119_0118 (CNCM I-4279 filed Feb. 25, 2010) [B)-B3)], for use in:

treatment and/or prevention of an intestinal disorder, preferably treatment and/or prevention of an intestinal motility disorder, or treatment and/or prevention of a disorder selected form the group consisting of constipation and IBS-C, or treatment and/or prevention of a disorder selected from the group consisting of diarrhoea, intestinal infection, IBS-D, IBS-PI, and IBD, or treatment and/or prevention of a disorder selected from the group consisting of IBS and IBD, or treatment and/or prevention of disorders found in elderly people, infants, or obese people, typically when administered in vivo to a subject.

In the compositions of the invention, said strains can be used in the form of whole bacteria which may be living or not. Alternatively, they can be used in the form of a bacterial lysate or in the form of bacterial fractions; the bacterial fractions suitable for this use can be chosen, for example, by testing their properties of alleviating the effects on VIP levels and levels of ChAT nerves of the coculture model described in the present invention. Preferably the bacterial cells are present as living, viable cells.

The compositions of the invention can be in any form suitable for administration, in particular oral administration. This includes for instance solids, semi-solids, liquids, and powders. Liquid compositions are generally preferred for easier administration, for instance as drinks.

The composition can for example comprise at least $10^5$, preferably at least $1\times10^6$, cfu per g dry weight, of at least one strain of bacteria, preferably of strains of bacteria as mentioned above. These are preferably selected from the group consisting of lactobacilli and bifidobacteria.

When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Examples of the compositions of the invention are nutritional compositions, including food products and in particular dairy products.

The composition can be for example a dairy product, preferably a fermented dairy product. The administration in the form of a fermented dairy product has the additional advantage of low lactose levels, which is further beneficial for IBS. Optionally, other strains of lactic acid bacteria may be present. The fermented product can be present in the form of a liquid or present in the form of a dry powder obtained by drying the fermented liquid. Preferably the fermented product is a fresh product. A fresh product, which has not undergone severe heat treatment steps, has the advantage that bacterial strains present are in the living form. Preferably the fermented product is a dairy product, more preferably fermented milk and/or fermented whey. Preferably the nutritional composition is yoghurt, or fermented milk in set, stirred or drinkable form. Preferably the fermented product is a cheese. Preferably the fermented product is a fermented vegetable, such as fermented soy, cereals and/or fruits in set, stirred or drinkable forms.

Preferably the present nutritional composition is a baby food, an infant milk formula or an infant follow-on formula. Preferably the present composition is a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

A composition comprising a mix of at least one strain of lactic acid bacterium or *bifidobacterium* increasing ChAT nerves and at least one strain of lactic acid bacterium or *bifidobacterium* increasing VIP levels is preferred. Such a mix will advantageously have an improved effect on motility as well as on IEB.

A mix of at least one strain belonging to group B), preferably B3), and at least one strain belonging to group A), preferably A3), is preferred. Such a mix will advantageously have an improved effect on motility as well as on IEB.

Therefore the present invention also relates to compositions comprising:
at least one strain of bacteria selected from the group consisting of the following strains:
DN__116__0047 (CNCM I-4317 filed May 19, 2010) [B)-B3)],
DN__154__0067 (CNCM I-4320 filed May 19, 2010) [B)-B3)], and
DN__119__0118 (CNCM I-4279 filed Feb. 25, 2010)[B)-B3)]; and
at least one strain of bacteria selected from the group consisting of the following strains:
DN__173__010 (CNCM I-2494 filed Jun. 20, 2000) [A)-A3)],
DN__156__0032 (CNCM I-4321 filed May 19, 2010) [A)-A3)],
DN__156__007 (CNCM I-2219 filed May 31, 1999) [A)-A3)], and
DN__121__0304 (CNCM I-4318 filed May 19, 2010) [A)-A3)].

The compositions of the invention can also comprise one or more other strain(s) of lactic acid bacteria, probiotic or not, for instance one or more bacterial strain(s) selected from the genera *Lactobacillus, Lactococcus, Streptococcus*, and *Bifidobacteria*. In particular, this (these) other strain(s) can include one or more strain(s) of *Streptococcus thermophilus*, and/or one or more strain(s) of *Lactobacillus bulgaricus*.

Application

In one embodiment strains of the present invention were found to increase the number of ChAT nerves. Choline acetyltransferase EC 2.3.1.6 is an enzyme that is synthesized within the body of a neuron and transferred to the nerve terminal. The role of choline acetyltransferase is to join Acetyl-CoA to choline, resulting in the formation of the neurotransmitter acetylcholine. It is used as an immunohistochemical marker for motor neurons. The effects on the ChAT nerve result in the improved contractions resulting in improved peristalsis. Therefore, the strains and compositions of the present invention able to increase ChAT nerves are advantageously administered to improve the ENS, to improve or enhance peristalsis, to improve intestinal motility and/or to decrease the gastrointestinal transit time. Increasing cholinergic phenotype is of therapeutic interest in GI pathologies associated with inhibition of colonic transit. In particular, various studies have shown that slow transit could be associated with a reduced expression of ChAT neurons. In particular, (i) severely constipated patients generally have a lower amount of ChAT nerves, (ii) the production of myenteric ACh significantly decreased both during the course of infection and post infection (PI), (iii) during aging a reduction of the proportion of cholinergic neurons has been reported.

In this context, using strains of bacteria, preferably lactic acid bacteria or bifidobacteria to enhance cholinergic expression in neurons could be of future therapeutically interest for severely constipated patient and IBS-C. Therefore, the strains and compositions of the present invention are advantageously administered to patients suffering from IBS-C, and/or constipation. Strains that are most useful are the group B) or B3) strains mentioned above.

In one particular embodiment the strains and compositions of the present invention are used by or for elderly people. Elderly people in the present invention are defined as human with an age above 65 years, preferably above 70 years, preferably above 75 years, preferably above 80 years, preferably above 85 years. Elderly people typically have decreased number of ChAT neurons in the enteric nervous system located in the colon, most preferably in the transversal colon. Therefore, the strains and compositions of the present invention are advantageously administered to treat and/or prevent IBS, preferably IBS-C, and/or constipation for elderly people. Strains able to increase ChAT nerves are group B), such as strain DN__154__0067 (CNCM I-4320 filed May 19, 2010), DN__116__0047 (CNCM I-4317 filed May 19, 2010) and DN__119__0118 (CNCM I-4279 filed Feb. 25, 2010). They preferably do not decrease VIP, since VIP is necessary for a good IEB function and for relaxation of the GI tract, another important part of the GI tract motility such as peristalsis. The strains meeting this criterion were DN__154__0067 (CNCM I-4320 filed May 19, 2010), and DN__116__0047 (CNCM I-4317 filed May 19, 2010). However, also strain DN__119__0118 (CNCM I-4279 filed Feb. 25, 2010) did not negatively affect IEB function as determined by TEER experiments, as TEER did not decreased.

In one embodiment the strains of the present invention were found to increase the levels of VIP. With respect to the digestive system, VIP induces smooth muscle relaxation (lower oesophageal sphincter, stomach, gallbladder), stimulates secretion of water into pancreatic juice and bile, and causes inhibition of gastric acid secretion and absorption from the intestinal lumen. Its role in the intestine is to greatly stimulate secretion of water and electrolytes, as well as dilating intestinal smooth muscle, dilating peripheral blood vessels, stimulating pancreatic bicarbonate secretion, and inhibiting gastrin-stimulated gastric acid secretion. These effects work together to increase motility. Therefore this finding is indicative for these strains to have an improved effect on intestinal motility, in particular the relaxation part of motility. VIP also beneficially increases IEB function. Therefore, the strains and compositions of the present invention are advantageously administered to improve the ENS, to improve or enhance peristalsis, to decrease permeability, to improve intestinal motility and/or to decrease the gastro-intestinal transit time. Therefore, the strains and compositions of the present invention are advantageously administered for use in or to patients suffering from:

- treatment and/or prevention of an intestinal disorder, preferably treatment and/or prevention of an intestinal motility disorder, or
- treatment and/or prevention of a disorder selected form the group consisting of constipation and IBS-C, or
- treatment and/or prevention of a disorder selected from the group consisting of diarrhoea, intestinal infection, IBS-D, IBS-PI, and IBD, or
- treatment and/or prevention of a disorder selected from the group consisting of IBS and IBD, or
- treatment and/or prevention of disorders found in elderly people, infants, and obese people.

Strains that are most useful are the group A) or A3) strains mentioned above. Details or advantages of the present invention can be found in the non limitative examples below.

EXAMPLES

Example 1

Screening of Probiotic in a Co-Culture Model Involving Epithelial Cells and Enteric Neuronal Cells Cell Culture Pregnant Sprague-Dawley rats were purchased (CERJ, Le Genest St Isle, France and Janvier-Breeding Center, Belgium) and killed by an overdose of $CO_2$ followed by severing the carotid arteries. The embryos (35-45 per isolation from 3 pregnant rats) were removed and killed by decapitation. The small intestines of embryos were removed and finely diced in HBSS (Sigma, France). Tissue fragments were collected in 5 ml of medium (DMEM-$F_{12}$ 1:1 medium) and digested at 37° C. for 15 min in 0.1% trypsin (Sigma). The trypsin reaction was stopped by adding 10 ml of medium containing 10% foetal calf serum and then treated by DNAse I (0.01%, Sigma) for 10 min at 37° C. After triturating with a 10 ml pipette, cells were centrifuged at 750 r.p.m. for 10 min. Cells were counted and then seeded at a density of $2.4 \times 10^5$ cells/cm² on 24 well plates previously coated for 6 h with a solution of gelatine (0.5%, Sigma) in sterile phosphate buffered saline (PBS). After 24 h, the medium was replaced with a serum free medium (DMEM-F12 1:1 containing 1% of N-2 supplement (Life technologies, France). Cells were maintained in culture for 14 days to obtain primary culture of enteric nervous system (ENS). Half of the medium was replaced every other day. At 14 days the primary neuronal cells were ready for the establishment of the co-culture model.

T84 cell line (EATCC) was cultured in DMEM-F12 (1:1, GIBCO) supplemented with 10% heat inactivated FBS and 50 IU/ml penicillin and 50 µg/ml streptomycin. Cells were seeded in 12-well Transwell® filters (Corning, N.Y. USA) at a density of $2 \times 10^5$ cells/insert and cultured to obtain confluence.

One day after epithelial cells arrived to confluence, Transwell® filters were transferred in the 12-well plates seeded at the bottom with enteric nervous cells. Epithelial and neuronal cells were co-cultured in the medium for epithelial cells.

Growing of Strains of Bacteria

Bacteria were grown for 16 hrs in TGYH for bifidobacteria and lactobacilli, except for strain DN_173_010 (CNCM I-2494 filed Jun. 20, 2000) which was grown on MRS+cysteine medium, washed in PBS twice and adjusted to $4.10^8$ cfu/ml in order to add consistently the same volume of bacterial suspension to the filter. The strains were added in the filter compartment at a MOI of 40 bacteria/epithelial cell. As a control, no bacteria were added.

After 8 hrs of co-incubation, the filter compartment containing epithelial cells and bacteria was removed and primary neuronal cells were incubated for 24 h in a humidified incubator containing 5% $CO_2$. In the control wells neuronal cells where stimulated with 1 mM butyrate and 40 mM KCl when ChAT and VIP measurements were performed, respectively.

Immunohistochemical Staining. Measuring ChAT Nerves

After the incubation, immunohistochemistry was performed to detect neuronal cell populations. After cells fixation (in 0.1 M PBS containing 4% paraformaldehyde for 1 h at room temperature), cells were washed 3 times in PBS, then permeabilized for 30 min in PBS/$NaN_3$ containing 0.5% Triton X-100 and 4% horse serum. Primary antibody: rabbit anti-neurone specific enolase (NSE) (1:2000; Biovalley, France) and rabbit anti-choline acetyl transferase was diluted in PBS/$NaN_3$, 0.5% Triton X-100 and 4% horse serum and incubated overnight at room temperature. After incubation with primary antiserum, cells were washed 3 times with PBS and incubated for 3 h with donkey anti-rabbit IgG conjugated to fluoresceine isothiocyanate (FITC) (1:200 Immunotech, France) and 7-amino-4-methyl-coumarin-3-acetate respectively. Specimens were viewed under an Olympus IX50 fluorescence microscope fitted with white video camera (Mod. 4910, Cohu Inc, Germany) connected to macintosh computer through a frame grabber card (Scion Image, SL Microtest).

VIP Measurements:

For VIP determination, neuronal cells were collected from the 12-well plates, the proteins were extracted using RIPA lysis buffer (Millipore, France) containing protease inhibitor cocktail (Roche Diagnostics, France) and VIP levels were measured by ELISA (Bachem, Germany).

Results

Differential response of primary enteric neurones on VIP and ChAT markers following interaction of some of 102 probiotic strains including lactic acid bacteria and Bifidobacteria are shown in Table 1. Only some strains belonging to group A3) or B3) or C3) are shown. Additionally it is mentioned that 26 strains were shown to have no significant effect on VIP and ChAT (including strains *Bifidobacterium longum* NCC 2705 (CNCM I-2618), *Lactobacillus rhamnosus* GG (ATCC 53103) and *Lactobacillus casei* Shirota), 11 strains belonging to group C2) were shown to decrease both VIP and ChAT (including strain *Bifidobacterium longum* W11 of Alfa-Wass (LMG P-21586)), 10 strains decreased VIP and had no effect on ChAT (including bench mark strains *Bifidobacterium infantis* UCC35264, *Bifidobacterium longum* Bb536, *Bifidobacterium animalis* spp *lactis* Bb12 (DSM 15954), and *Bifidobacterium animalis* spp *lactis* Bi-07 (ATCC SD5220) and 41 strains belonging to group C3) decreased ChAT and had no effect on VIP including strains *Lactobacillus johnsonii* LaI (CNCM I-1225), *Lactobacillus plantarum* 299v (DSM 9843) *Lactobacillus reuteri* SD 2122 (ATCC 55730)).

TABLE 1

Effect of incubation with lactic acid bacteria and bifidobacteria on VIP and ChAT levels in a coculture model with epithelial cell monolayer and primary ENS cells.

| | | VIP | | | ChAT | | |
|---|---|---|---|---|---|---|---|
| Group | DN Number species (CNCM number) | Estimated difference* vs control | p value | Empiric mean | Estimated difference vs control | p value | Empiric Mean |
| 1 | DN_154_0067 (CNCM I-4320 filed May 19, 2010) Bifidobacterium bifidum | −0.0097 | 0.9 | 0.0790 | 0.2709 | 0.09 | 0.1796 |
| 1 | DN_116_0047 (CNCM I-4317 filed May 19, 2010) Lactobacillus rhamnosus | −0.0389 | 0.7 | 0.0397 | 0.3151 | 0.10 | 0.2535 |
| 1 | DN_119_0118 (CNCM I-4279 Filed Feb. 25, 2010) Lactobacillus acidophillus | −0.1329 | 0.09 | −0.2221 | 0.2847 | 0.02 | 0.2796 |
| 2 | DN_173_010 (CNCM I-2494 filed Jun. 20, 2000) Bifidobacterium lactis | 0.2345 | 0.01 | 0.2001 | −0.2615 | 0.05 | −0.0825 |
| 2 | DN_156_0032 (CNCM I-4321 filed May 19, 2010) Bifidobacterium breve | 0.2248 | 0.01 | 0.2020 | −0.5450 | 0.00 | −0.5723 |
| 2 | DN_156_007 (CNCM I-2219 filed May 31, 1999) Bifidobacterium breve | 0.2715 | 0.02 | 0.3552 | −0.3632 | 0.01 | −0.1281 |
| 2 | DN_121_0304 (CNCM I-4318 filed May 19, 2010) Lactobacillus plantarum | 0.5976 | 0.00 | 0.6813 | −0.6269 | 0.00 | −0.3918 |

*Values are given as a difference compared to the control, where no bacterial strains were added.

Although strain DN_119_0118 (CNCM I-4279 filed Feb. 25, 2010) decreases VIP levels, it turned out with a TEER model (Hirotani et al, 2008, Yakugaku Zasshi Sep. 128(9): 1363-8) that incubation with the strain for 4 or 6 h did not significantly reduce TEER values, even in presence of damage vs. control. In short, bacteria were cultured in TGYH. The culture suspensions were washed with PBS. Subsequently, the bacteria (100 cfu/cell) were added to the apical side of the T84 cell monolayers. After 2 h incubation, LPS (L4516,—EPEC-0127: B8) was added on the apical side at 40 ng/ml or not added. Then, after 2 h and 4 h incubation, the TEER value was measured to assess epithelial barrier function. All experiments were performed three times independently and in triplicate in presence and in absence of LPS. The value of the T84 at t=0 was set at 100%. In the absence of LPS TEER at T4 was 98.7% and at T6 100.2% with strain DN_119_0118 (CNCM I-4279 filed Feb. 25, 2010); for T84 alone this was still 100%. In the presence of LPS the control T84 at T4 was 56.2% compared to t=0 and with strain DN_119_0118 (CNCM I-4279 filed Feb. 25, 2010) 47.9%; At T6 the T84 control was 46.7% and with strain DN_119_0118 (CNCM I-4279 filed Feb. 25, 2010) 52.2%.

Using this same TEER model especially strain DN_173_010 (CNCM I-2494 filed Jun. 20, 2000), DN_156_007 (CNCM I-2219 filed May 31, 1999), DN_121_0304 (CNCM I-4318 filed May 19, 2010) and DN_156_0032 (CNCM I-4321 filed May 19, 2010), all belonging to group A3), showed good results on the intestinal barrier function as assessed by TEER in presence of LPS. See Table 2.

TABLE 2

TEER results in presence of LPS of selected bacteria showing the best results

| | | TEER T4/TEER T0 (%) | | TEER T6/TEER T0 (%) | |
|---|---|---|---|---|---|
| Strain | | Signifi-cance | Empiric mean | Signifi-cance | Empiric mean |
| T84 control | | | 56.20 | | 46.76 |
| DN_173_010 (CNCM I-2494 filed Jun. 20, 2000) | B. lactis | *** | 71.27 | *** | 51.03 |
| DN_156_007 (CNCM I-2219 filed May 31, 1999) | B. breve | *** | 70.70 | *** | 55.87 |
| DN_121_0304 (CNCM I-4318 filed May 19, 2010) | L. plantarum | *** | 65.84 | *** | 64.37 |
| DN_156_0032 (CNCM I-4321 filed May 19, 2010) | B. breve | *** | 84.44 | *** | 80.38 |

*** p value < 0.05

The invention claimed is:

1. A fermented milk food product composition comprising at least one strain of isolated bacteria selected from the group consisting of:
   DN_156_0032 deposited under Accession No. I-4321 with Collection Nationale De Cultures De Micro-Organismes (CNCM) on May 19, 2010,
   DN_121_0304 deposited under Accession No. I-4318 with CNCM on May 19, 2010,
   DN_116_047 deposited under Accession No. I-4317 with CNCM on May 19, 2010, and
   DN_154_0067 deposited under Accession No. I-4320 with CNCM on May 19, 2010.

2. The composition according to claim 1 wherein:
   the at least one strain of bacteria is present in an amount effective which increases Choline AcetylTransferase (ChAT) levels in the enteric nervous system, and increases vaso-active intestinal peptide (VIP) levels in the enteric nervous system.

3. The composition according to claim 2, comprising:
at least one strain of bacteria selected from the group consisting of the following strains:
DN__116__047 (CNCM I-4317 filed May 19, 2010),
DN__154__0067 (CNCM I-4320 filed May 19, 2010), and
DN__119__0118 (CNCM I-4279 filed Feb. 25, 2010); and
at least one strain of bacteria selected from the group consisting of the following strains:
DN__173__010 (CNCM I-2494 filed Jun. 20, 2000),
DN__156__0032 (CNCM I-4321 filed May 19, 2010),
DN__156__007 (CNCM I-2219 filed May 31, 1999), and
DN__121__0304 (CNCM I-4318 filed May 19, 2010).

4. The composition according to claim 1, wherein the composition comprises at least $10^5$ CFU per gram dry weight of the at least one strain of bacteria.

5. The composition according to claim 1, wherein the fermented milk food product is a yogurt.

6. A method of:
A. increasing vaso-active intestinal peptide (VIP) levels of the enteric nervous system, or
B. increasing Choline AcetylTransferase ImmunoReactive neurones (ChAT) levels of the enteric nervous system, or
C. decreasing ChAT levels of the enteric nervous system, comprising administering to a subject the composition of claim 1.

7. The method according to claim 6, wherein said composition:
A3. increases VIP, provided that ChAT is not increased, or
B3. increases ChAT, provided that VIP is not increased, or
C3. decreases ChAT, provided that VIP is not decreased, or
C2. decreases ChAT and decreases VIP.

8. The method according to claim 6, wherein said composition is administered to the subject for:
treatment and/or prevention of an intestinal disorder, or
treatment and/or prevention of a disorder selected from the group consisting of constipation and IBS-C, or
treatment and/or prevention of a disorder selected from the group consisting of diarrhoea, intestinal infection, IBS-D, IBS-PI, and IBD, or
treatment and/or prevention of a disorder selected from the group consisting of IBS and IBD, or
treatment and/or prevention of disorders found in elderly people, infants, and obese people.

9. The method according to claim 6, wherein said composition:
A. increases VIP levels of the enteric nervous system, and is used in treatment and/or prevention of an intestinal disorder, or
B. increases ChAT levels of the enteric nervous system, and is used in treatment and/or prevention of a disorder selected form the group consisting of constipation and IBS-C, or
C. decreases ChAT levels of the enteric nervous system, and is used in treatment and/or prevention of a disorder selected from the group consisting of diarrhoea, IBS-D, IBS-PI, IBD.

10. The method according to claim 6, wherein said composition:
A3. increases VIP provided that ChAT is not increased, and is administered to a subject for:
treatment and/or prevention of a disorder selected from the group consisting of IBS and IBD, or
treatment and/or prevention of disorders found in elderly people, infants, or obese people.

11. The method according to claim 6, wherein said composition:
B3. increases ChAT, provided that VIP is not increased, and is administered to a subject for treatment and/or prevention of a disorder selected form the group consisting of constipation and IBS-C.

12. The method according to claim 6, wherein said composition:
C3. decreases ChAT, provided that VIP is not decreased, and is administered to a subject for treatment and/or prevention of a disorder selected form the group consisting of constipation and IBS-C.

13. The method according to claim 6, wherein said composition:
C2. decreases ChAT and decreases VIP, and is administered to a subject for treatment and/or prevention of a disorder selected from the group consisting of diarrhoea, intestinal infections, IBS-D, IBS-PI, and IBD.

14. The method according to claim 6, wherein the strain of bacteria is selected from the group consisting of the following strains:
DN__173__010 (CNCM 1-2494 filed Jun. 20, 2000),
DN__156__0032 (CNCM 1-4321 filed May 19, 2010),
DN__156__007 (CNCM 1-2219 filed May 31, 1999),
DN__121__0304 (CNCM 1-4318 filed May 19, 2010),
DN__116__047 (CNCM 1-4317 filed May 19, 2010),
DN__154__0067 (CNCM 1-4320 filed May 19, 2010), and
DN__119__0118 (CNCM 1-4279 filed Feb. 25, 2010).

15. A method of treating a subject comprising administering the composition of claim 1,
wherein the composition is administered to a subject for:
treatment and/or prevention of an intestinal disorder, or
treatment and/or prevention of a disorder selected from the group consisting of constipation and IBS-C, or
treatment and/or prevention of a disorder selected from the group consisting of diarrhoea, intestinal infection, IBS-D, IBS-PI, and IBD, or
treatment and/or prevention of a disorder selected from the group consisting of IBS and IBD, or
treatment and/or prevention of disorders found in elderly people, infants, or obese people.

16. The method according to claim 15, wherein the strain of bacteria is selected from claim 1,
and the composition is administered to the subject for:
treatment and/or prevention of a disorder selected from the group consisting of IBS and IBD, or
treatment and/or prevention of disorders found in elderly people, infants, or obese people.

17. The method according to claim 15, wherein
the strain of bacteria is selected from claim 1,
and the composition is administered to the subject for treatment and/or prevention of a disorder selected form the group consisting of constipation and IBS-C.

18. The method according to claim 15, comprising
at least one strain of bacteria selected from claim 1,
wherein said composition is administered to the subject for:
A. increasing vaso-active intestinal peptide (VIP) levels of the enteric nervous system, provided that ChAT is not increased.

19. The method according to claim 18, wherein said composition is administered to a subject for:
treatment and/or prevention of a disorder selected from the group consisting of IBS and IBD, or
treatment and/or prevention of disorders found in elderly people, infants, or obese people.

20. The method according to claim 15, comprising
at least one strain of bacteria selected from claim 1,
wherein said composition is administered to the subject for:
B. increasing ChAT levels of the enteric nervous system.

21. The method according to claim 20, wherein said composition is administered to the subject for treatment and/or prevention of a disorder selected from the group consisting of constipation and IBS-C.

22. The method according to claim 15, wherein said composition is administered to the subject for improving gastrointestinal motility, improving intestinal peristalsis and/or decreasing intestinal permeability.

23. A method of treating a disorder in a subject comprising administering the composition of claim 1,
wherein the subject is suffering from a disorder selected from the group consisting of:
constipation, IBS-C,
diarrhoea, intestinal infection, IBS-D, IBS-PI, IBD, IBS, and
disorders found in elderly people, infants, or obese people.

* * * * *